US 6,737,460 B2

(12) United States Patent
Doisaki et al.

(10) Patent No.: US 6,737,460 B2
(45) Date of Patent: *May 18, 2004

(54) VINYL MONOMERS HAVING POLYENIC SIDE CHAINS DERIVED FROM HIGHLY UNSATURATED FATTY ACIDS AND DERIVATIVES THEREOF, AND POLYMERS OF SAID MONOMERS

(75) Inventors: Nobushige Doisaki, Tokyo (JP); Shuji Jinno, Tokyo (JP); Kazuhiko Hata, Tokyo (JP); Takeshi Endo, Kanagawa (JP)

(73) Assignee: Nippon Suisan Kaisha, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/101,836

(22) PCT Filed: Jan. 16, 1997

(86) PCT No.: PCT/JP97/00068

§ 371 (c)(1),
(2), (4) Date: Jul. 17, 1998

(87) PCT Pub. No.: WO97/26239

PCT Pub. Date: Jul. 24, 1997

(65) Prior Publication Data

US 2001/0003128 A1 Jun. 7, 2001

(30) Foreign Application Priority Data

Jan. 19, 1996 (JP) .............................. 8-026164

(51) Int. Cl.$^7$ ................................. C08K 5/09
(52) U.S. Cl. ................ 524/322; 524/556; 524/601; 526/320; 549/313; 554/18; 554/174; 554/175; 564/402
(58) Field of Search ............... 525/68, 74, 77; 526/319, 320, 321; 524/322, 556, 601; 549/313; 564/402; 554/18, 174, 175

(56) References Cited

U.S. PATENT DOCUMENTS

| 3,284,385 A | 11/1966 | D'Alelio ................ 260/23 |
| 3,287,298 A | 11/1966 | D'Alelio ................ 260/23 |
| 4,145,320 A | 3/1979 | Ferruti et al. .......... 260/23 AR |
| 4,311,624 A | * 1/1982 | Emmons et al. |
| 5,061,753 A | * 10/1991 | Maruyama et al. .......... 525/68 |
| 5,160,738 A | * 11/1992 | Macaulay et al. .......... 424/401 |
| 5,173,113 A | 12/1992 | Sugerman et al. .......... 106/27 |
| 5,746,925 A | * 5/1998 | Alper ...................... 210/728 |

FOREIGN PATENT DOCUMENTS

| JP | 57190016 A | * 11/1982 |
| JP | 62-95525 | 5/1987 |
| JP | 8-34826 | 2/1996 |
| JP | 8-82925 | 3/1996 |

OTHER PUBLICATIONS

Polyakova, M.N., "Film formation of a mixed ester of ethylene glycol with linolenic and methacrylic acids", Lakokras. Mater. Ikh Primen., (1987), No. 4, P5–6, Chemical Abstracts vol. 108, Column 39673.

Fung Bor Chen, "Crosslinkable emulsion polymers by autoxidation II", Journal of Applied Polymer Science, vol. 30, No. 12, P4551–4570 (1985).

* cited by examiner

*Primary Examiner*—Tatyana Zalukaeva
(74) *Attorney, Agent, or Firm*—Westerman, Hattori, Daniels & Adrian, LLP

(57) ABSTRACT

Vinyl monomers having polyenic side chains derived from highly unsaturated fatty acids represented by the general formula: $R_1COOH$ wherein $R_1$ is a $C_{19-24}$ hydrocarbon having 5 or 6 unsaturated bonds, and the derivatives thereof. Vinyl monomers having polyenic side chains derived from highly polyunsaturated fatty acids and the polymers of said monomers can be provided. In addition polymers having double bonds in the side chain into which various functional groups can be introduced can be provided. Useful utilization of fatty acid esters remaining as the residue in distillation of fish oil can be provided.

30 Claims, 1 Drawing Sheet

VINYL MONOMERS HAVING POLYENIC SIDE CHAINS DERIVED FROM HIGHLY UNSATURATED FATTY ACIDS AND DERIVATIVES THEREOF, AND POLYMERS OF SAID MONOMERS

FIELD OF THE INVENTION

This invention relates to the novel compounds, vinyl monomers having polyenic side chains derived from highly unsaturated fatty acids and (co)polymers thereof.

BACKGROUND OF THE INVENTION

Vinyl monomers having various functional groups in the side chains are known. Polymerization behavior of these monomers based on the functional groups and the relation between the structure and the properties of the resultant polymers are subjects of interest. As a particular use thereof a method for production of a polymer containing polyunsaturated acid residues is described, for example, in Japanese Published Unexamined Patent Application (KOKAI TOKKYO KOHO) No. 125497/76; graft polymerization of poly(acrylic acid) and poly(methacrylic acid) with a poly (fatty acid) through ester bonding or amide bonding was performed to test whether the graft copolymer is usable as a DDS of prostaglandin. The graft polymerization with a polymer elongated the duration of action of prostaglandin as compared with prostaglandin used alone.

The report in J. Appl. Poly. Sci., 30, 4571–4582 (1985) describes the synthesis of lauryl acrylate (LA), oleyl acrylate (OA), linoleyl acrylate (LA2), and linolenyl acrylate (LA3) from each corresponding fatty acid and the reactivity thereof. The subsequent report in J. Appl. Poly. Sci., 30, 4551–4570 (1985) describes the synthesis of the crosslinked products of the copolymers reported in the preceding paper (making use of the double bonds in the fatty acids) and the physical properties of the products. The crosslinked products were obtained more rapidly in the presence of a cobalt catalyst than in the presence of a lead catalyst, and could be obtained even without any catalyst though it took more time. Physical parameters determined included tension, glass transition temperature, and molecular weight, all of which were reported to be more desirable with copolymers with LA incapable of crosslinking. Thus the reaction of a fatty acid with a vinyl compound itself is known, but there is no report on the experiments with highly unsaturated fatty acids such as EPA and DHA. Namely no report has been published on vinyl monomers having polyenic side chains derived from highly unsaturated fatty acids and the derivatives thereof, and the polymers of said monomers, and the method for production of said monomers and polymers.

Eicosapentaenoic acid (abbreviated as EPA somewhere hereinafter) and docosahexaenoic acid (abbreviated as DHA somewhere hereinafter), contained as they are or in the form of derivatives such as glycerides in natural fat and oil, particularly in fat and oil in marine products such as mackerel, sardine, and cod, have recently become available in highly purified forms.

However, natural fat and oil including fish oil contain, in addition to EPA having 20 carbon atoms and 5 double bonds in a molecule and DHA having 22 carbon atoms and 6 double bonds in a molecule, other various fatty acids having 12 to 24 carbon atoms and 0 to 6 double bonds in each molecule abundantly. Thus, the fatty acids, usually the esters thereof, remaining as the residue in distillation may remain behind when highly purified products are to be produced from the fatty acid mixtures described above as the starting material.

It is desirable to develop a useful method for utilizing the residue in distillation, the residue which is substantially a mixture of highly unsaturated fatty acid esters.

DISCLOSURE OF THE INVENTION

The object of this invention is to provide novel vinyl monomers of a type unknown from the vinyl monomers developed so far. Another object of this invention is to provide polymers having double bonds in the side chains into which various functional groups can be introduced. A further object of this invention is to provide novel vinyl monomers having polyenic side chains derived from highly unsaturated fatty acids and the derivatives having double bonds in the side chains into which various functional groups can be introduced. A further object of this invention is to provide novel vinyl monomers having polyenic side chains derived from highly unsaturated fatty acids and the derivatives thereof and the polymers of said monomers. Yet another object of this invention is to provide a useful method for utilizing the fatty acid esters remaining as the residue in the distillation of esterified fish oil.

Vinyl monomers having polyenic side chains derived from highly unsaturated fatty acids represented by the general formula (1):

$$R_1COOH \qquad (1)$$

wherein $R_1$ is a $C_{19\text{-}24}$ hydrocarbon having 5 or 6 unsaturated bonds, and the derivatives thereof.

Highly unsaturated fatty acids represented by the general formula (1) are exemplified by eicosapentaenoic acid, docosapentaenoic acid, docosahexaenoic acid, hexadecatetraenoic acid, octatetraenoic acid, eicosatetraenoic acid, docosatetraenoic acid and/or fatty acids derived from fatty acid esters remaining as the residue in the distillation of esterified fish oil.

Derivatives of highly unsaturated fatty acids represented by the general formula (1) are exemplified by eicosapentaenol, docosapentaenol, docosahexaenol, hexadecatetraenol, octatetraenol, eicosatetraenol and/or docosatetraenol. Derivatives of highly unsaturated fatty acids used in this invention are exemplified by fatty acid esters remaining as the residue in the distillation of esterified fish oil or alcohols derived therefrom.

Vinyl monomers to bind highly unsaturated fatty acids represented by the general formula (1) or the derivatives thereof are exemplified by methacrylic acid, methacrylic acid esters, acrylic acid, acrylic acid esters, ethylene, butadiene, vinyl chloride, vinyl acetate, styrene, and acrylonitrile; that is, monomers having vinyl group that are used as starting materials for production of polymers are used.

Vinyl monomers in this invention are preferably those obtained by esterification of eicosapentaenoic acid, docosapentaenoic acid, docosahexaenoic acid and/or fatty acids derived from fatty acid esters remaining as the residue in the distillation of esterified fish oil, with 2-hydroxyethyl methacrylate. Other preferable examples are vinyl monomers obtained by esterification of eicosapentaenol, docosapentaenol, docosahexaenol and/or alcohols derived from fatty acid esters remaining as the residue in the distillation of esterified fish oil, with acrylic acid and/or methacrylic acid.

A vinyl monomer in this invention can be prepared by, e.g. reducing docosahexaenoic acid (DHA) into an alcohol either directly or through several reaction steps and reacting the alcohol with acryloyl chloride. These vinyl monomers can be polymerized by the use of various polymerization initiators. In addition the vinyl monomers can be copolymerized with other monomers.

Polymerization initiators used are preferably those known as radical polymerization initiators such as azobisisobutyronitrile (abbreviated as AIBN somewhere hereinafter), benzoyl peroxide, acetyl peroxide, etc.

Polymerization may be carried out in the solid phase (bulk polymerization) or in the liquid phase by using a reaction solvent such as chlorobenzene, dimethylformamide, or methanol.

BRIEF DESCRIPTION OF DRAWING

The drawing illustrates the $^1$H-NMR chart of the polymer obtained in Example 5.

BEST EMBODIMENTS OF THE INVENTION

Figure 1:
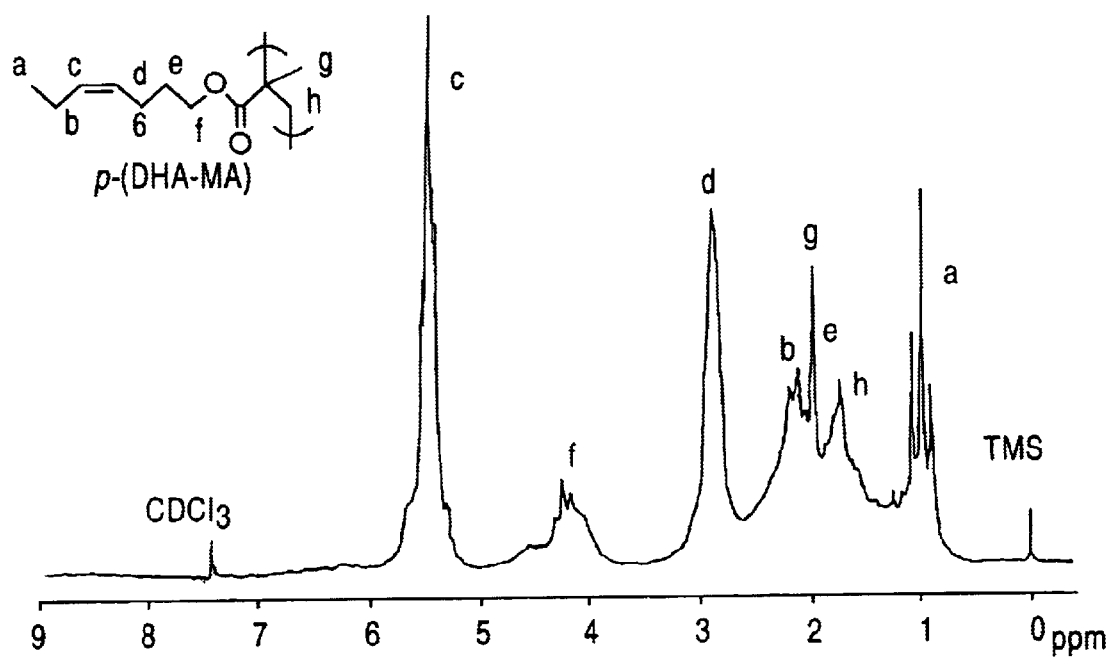

The invention is illustrated in more detail in the following examples. This invention is not limited at all by these examples.

EXAMPLE 1

Synthesis of 2-(docosahexaenyloxy)ethyl methacrylate (abbreviated as DHA-HEMA somewhere hereinafter)

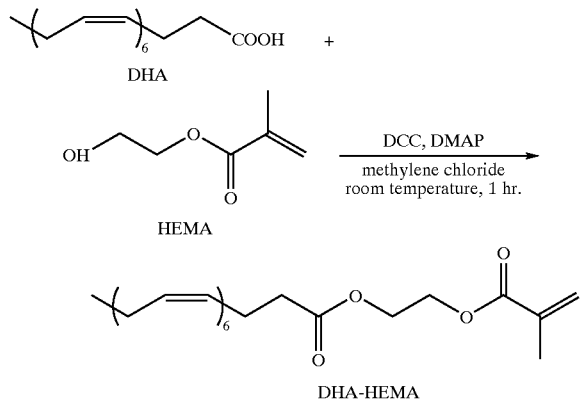

To the mixture of DHA (986 mg, 3 mmol) and 2-hydroxyethyl methacrylate (abbreviated as HEMA somewhere hereinafter) (390 mg, 3 mmol), was added dropwise over 10 minutes under ice-cold condition 10 ml of the solution of N,N'-dicyclohexylcarbodiimide (abbreviated as DCC somewhere hereinafter) (619 mg, 3 mmol) and 4-dimethylaminopyridine (abbreviated as DMAP somewhere hereinafter) (367 mg, 3 mmol) in methylene chloride. After dropwise addition the mixture was stirred at room temperature for one hour, and the resultant urea derivative of DCC was collected by filtration, washed with 3% aqueous hydrochloric acid (10 ml×3), and dried (anhydrous magnesium sulfate), followed by evaporation of methylene chloride and purification of the residual liquid by silica gel open column chromatography (ethyl acetate:hexane=1:20). Yield: 1.0235 g (77.4% yield).

The results of IR spectroscopy and 90 MHz $^1$H-NMR spectroscopy of DHA-HEMA are as follows:

1. IR (neat cm$^{-1}$)
    3014, 2965, 2932, 1742, 1725, 1640, 1152, 712
2. $^1$H-NMR (90 MHz, CDCl$_3$, δ in ppm)
    0.97 (3H, t, J=7.5 Hz),
    1.92–2.29) (2H,m), 1.94 (3H, s),
    2.30–2.50 (4H,m), 2.56–3.12(10H,m),
    4.22–4.45 (4H,m), 5.06–5.62 (12H,m),
    5.45–5.70 (1H,m), 6.02–6.20 (1H,m)

EXAMPLE 2

Synthesis of docosahexaenyl methacrylate (abbreviated as DHA-MA somewhere hereinafter)

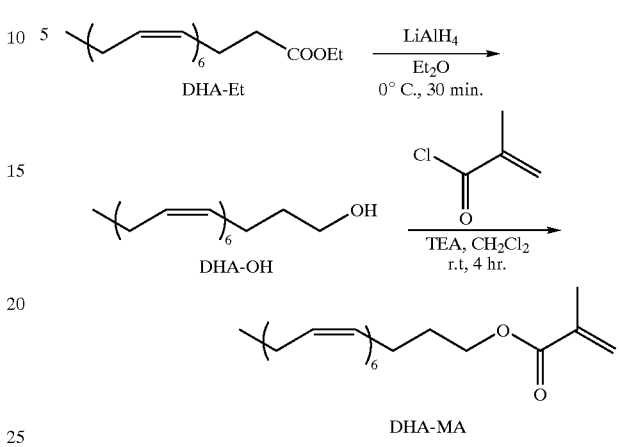

1.28 g (33.7 mmol) of lithium aluminum hydride (LiAlH$_4$) and 100 ml of anhydrous dietylether were placed into an eggplant-shape flask of which air had been replaced by argon gas, and kept at 0° C. To the mixture was added dropwise over about 30 minutes the solution of 10 g (28.1 mmol) of ethyl docosahexaenate in diethylether (20 ml of anhydrous diethylether), and then stirred at 0° C. for 30 minutes. After stirring, ethyl acetate and the saturated solution of sodium chloride were added to the reaction mixture, followed by removal of the precipitate by filtration. The filtrate was concentrated under reduced pressure, and purified by silica gel open column chromatography (hexane:ethyl acetate=5:1), to give 5.67 g of docosahexaenol (abbreviated as DHA-OH somewhere hereinafter).

0.5 g (1.6 mmol) of DHA-OH thus obtained, 516 μl of triethylamine (0.48 g, 4.77 mmol), and 10 ml of anhydrous methylene chloride were placed into an eggplant-shape flask of which air had been replaced by argon gas, and kept at 0° C. Into the mixture, was added dropwise the solution of 209 μl (0.22 g, 2.1 mmol) of methacryloyl chloride in anhydrous methylene chloride (6 ml). After dropwise addition, the reaction mixture was stirred for 4 hours at room temperature. On completion of the reaction the reaction mixture was washed with 1N aqueous hydrochloric acid and distilled water, and dried with anhydrous magnesium sulfate. The solvent was evaporated off under reduced pressure, and the residue was purified by silica gel open column chromatography (hexane:ethyl acetate=20:1), to give 0.45 g (1.2 mmol, 75% yield) of DHA-MA.

The results of IR spectroscopy and 90 MHz $^1$H-NMR spectroscopy of DHA-MA are as follows:

1. IR (neat, cm$^{-1}$)
    3014, 2965, 1723, 1640, 1160, 940
2. $^1$H-NMR (90 MHz, CDCl$_3$, δ in ppm)
    0.97 (3H, t, J=7.5 Hz),
    1.52–1.96 (2H,m), 1.94 (3H, S),
    1.82–2.32 (4H,m), 2.55–3.10 (10H,m),
    4.15 (2H,t, J=6.5 Hz).
    5.08–5.50 (12H, m), 5.40–5.61 (1H,m),
    6.00–6.12 (1H,m)

EXAMPLE 3

Synthesis of docosahexaenyl acrylate (abbreviated as DHA-AA somewhere hereinafter)

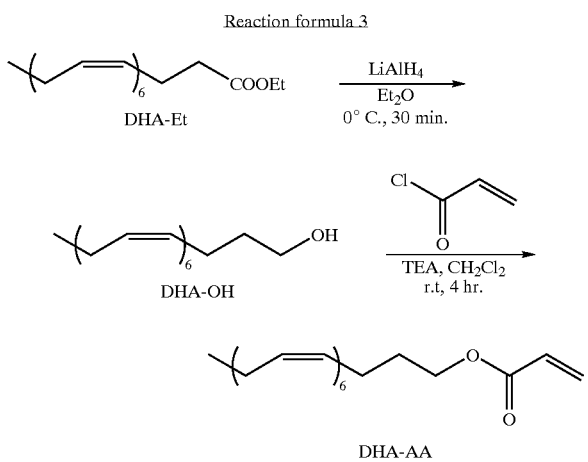

Reaction formula 3

The title compound was synthesized by using acryloyl chloride in the same manner as in Example 2.

The results of IR spectroscopy and 90 MHz $^1$H-NMR spectroscopy of DHA-AA are as follows:
1. IR (neat, cm$^{-1}$)
   3014, 2964, 1728, 1638, 1189, 986
2. $^1$H-NMR (90 MHz, CDCl$_3$, δ in ppm)
   0.95 (3H, t, J=7.4 Hz),
   1.49–1.88 (2H,m), 1.80–2.32 (4H, m),
   2.50–3.02 (10H,m),
   4.14 (2H, t, J=6.4 Hz),
   5.02–5.54 (12H,m), 5.48–6.54 (3H,m)

EXAMPLE 4

Polymerization of 2-(docosahexaenyloxy)ethyl methacrylate (DHA-HEMA)

To DHA-HEMA (3 mmol, 1.32 g) obtained in Example 1 was added 2,2-azobisisobutyronitrile (AIBN) to 3 mol %, and the container was degassed and sealed, followed by solid phase polymerization at 60° C. for 20 hours. After 20 hours, the conversion rate of DHA-HEMA was 13% as determined from $^1$H-NMR. Molecular weight and distribution of molecular weight of the polymers were determined by GPC with conversion to polystyrene basis. The results are summarized in Table 1.

EXAMPLES 5 TO 7

1 mmol of DHA-MA was subjected to solid phase polymerization (Example 5), or to liquid phase polymerization after dissolving in chlorobenzene to the concentration of 1 mol/l (Example 6), and 1 mmol of DHA-AA was subjected to solid phase polymerization (Example 7), in the same manner as in Example 4 with 10 mol % of AIBN added. The results are summarized in Table 1. The $^1$H-NMR chart of the polymer obtained in Example 5 is shown in FIG. 1.

TABLE 1

| | monomer | AIBN (mol %) | polymerization solvent | conversion rate (%) | molecular weight (Mn) | molecular weight distribution (Mw/Mn) |
|---|---|---|---|---|---|---|
| Example 4 | DHA-HEMA | 3 | none | 13 | 7900 | 1.20 |
| Example 5 | DHA-MA | 10 | none | 41 | 9400 | 3.66 |
| Example 6 | DHA-MA | 10 | chlorobenzene | 34 | 5000 | 1.80 |
| Example 7 | DHA-AA | 10 | none | 26 | 3000 | 3.11 |

EXAMPLES 8 AND 9

Copolymerization of DHA-HEMA with HEMA 1 mmol of DHA-HEMA and 1 mmol of HEMA were dissolved in N,N-dimethylformamide (Example 8) or chlorobenzene (Example 9) to the concentration of 1 mol/l, and subjected to liquid phase polymerization in the same manner as in Example 4. The content of p-DHA-HEMA in the resultant polymer was determined by $^1$H-NMR. The result is shown in Table 2.

TABLE 2

| | AIBN (mol %) | polymerization solvent | conversion rate (%) | molecular weight (Mn) | molecular weight distribution (Mw/Mn) | DHA-HEMA content (%) |
|---|---|---|---|---|---|---|
| Example 8 | 10 | N N-dimethylformamide | 47 | 6500 | 1.50 | 33 |
| Example 9 | 20 | chlorobenzene | 60 | 4900 | 2.37 | 36 |

INDUSTRIAL APPLICABILITY

Vinyl monomers having polyenic side chains derived from highly polyunsaturated fatty acids and the polymers of said monomers can be provided. Novel vinyl monomers of a type unknown from the conventional vinyl monomers developed so far can be provided. In addition polymers having double bonds in the side chain into which various functional groups can be introduced can be provided. Useful utilization of fatty acid esters remaining as the residue in distillation of fish oil can be provided.

What is claimed is:

1. Vinyl monomers having polyenic side chains derived from highly unsaturated fatty acids represented by the general formula (1):

$$R_1COOH \qquad (1)$$

wherein $R_1$ is a $C_{19}$–$C_{24}$ hydrocarbon having 5 to 6 unsaturated bonds, and the derivatives thereof.

2. Vinyl monomers in claim 1, wherein the highly unsaturated fatty acids represented by the general formula (1) are eicosapentaenoic acid, docosapentaenoic acid, docosahexaenoic acid, and/or fatty acids derived from fatty acid esters remaining as the residue in distillation of esterified fish oil.

3. Vinyl monomers of claim 1, wherein the derivatives of highly polyunsaturated fatty acids represented by the general formula (1) are fatty acid esters remaining as the residue in distillation of esterified fish oil.

4. Vinyl monomers of claim 2, wherein said monomers are obtained by esterification of highly unsaturated fatty acids represented by the general formula (1) with 2-hydroxyethyl methacrylate.

5. Vinyl monomers of claim 1, wherein the derivatives of highly unsaturated fatty acids represented by the general formula (1) are eicosapentaenol, docosapentaenol, docosahexaenol, and/or alcohols derived from fatty acid esters remaining as the residue of distillation of esterified fish oil, and said monomers are prepared by esterification of the above-mentioned compounds with acrylic acid and/or methacrylic acid.

6. Polymers obtained by polymerization of the vinyl monomer of claim 1.

7. Copolymers obtained by copolymerization of a vinyl monomer of claim 1 with another monomer.

8. Copolymers obtained by copolymerization of a vinyl monomer of claim 2 with another monomer.

9. Copolymers obtained by copolymerization of a vinyl monomer of claim 3 with another monomer.

10. Copolymers obtained by copolymerization of a vinyl monomer of claim 4 with another monomer.

11. Copolymers obtained by copolymerization of a vinyl monomer of claim 5 with another monomer.

12. Polymers obtained by polymerization of a vinyl monomer of claim 2.

13. Polymers obtained by polymerization of a vinyl monomer of claim 3.

14. Polymers obtained by polymerization of a vinyl monomer of claim 4.

15. Polymers obtained by polymerization of a vinyl monomer of claim 5.

16. A first vinyl compound, having general formula $R_1COOR_2$, wherein $R_1$ is a $C_{19}$–$C_{24}$ hydrocarbon having 5 or 6 double bonds and wherein $R_2$ comprises a vinyl group.

17. A composition of matter comprising the first vinyl compound of claim 16 and further comprising:

a second vinyl compound having the same general formula as the first vinyl compound, wherein said second vinyl compound is different from said first vinyl compound.

18. The composition of matter of claim 17, the composition being derived from a residue from distillation of esterified fish oil.

19. The first vinyl compound of claim 16, said group $R_2$ being 2-ethyl methacrylate.

20. The composition of matter of claim 17, said group $R_2$ being 2-hydroxyethyl methacrylate.

21. The composition of matter of claim 18, said composition being derived by esterification with 2-hydroxyethyl methacrylate.

22. The first vinyl compound of claim 19, said first vinyl compound being prepared by esterification of an acid selected from eicosapenataenoic acid, doxosapentaenoic acid, and docosahexaenoic acid.

23. A first vinyl ester having formula $R_1COOCH_2R_2$, wherein $R_2$ is a $C_{19}$–$C_{24}$ hydrocarbon having 5 or 6 double bonds and $R_1$ comprises a vinyl group.

24. The first vinyl ester of claim 23, wherein $R_1COO$ is the methacrylate or acrylate group.

25. The first vinyl ester of claim 23, said first vinyl ester being obtained by esterification of an alcohol produced by reduction of $R_2COOH$ or a derivative of $R_2COOH$.

26. The first vinyl ester of claim 23, said first vinyl ester being obtained by esterificatoin of an alcohol produced by reduction of an ester derivative of $R_2COOH$.

27. The first vinyl ester of claim 25, said $R_2COOH$ or a derivative of $R_2COOH$ being obtained from a residue from distillation of esterified fish oil.

28. The first vinyl ester of claim 26, said reduction being performed using lithium aluminum hydride.

29. A composition of matter obtained by polymerization of the first vinyl ester of claim 16.

30. A composition of matter obtained by polymerization of the first vinyl ester of claim 23.

* * * * *